United States Patent
Iizuka

(10) Patent No.: US 11,007,126 B2
(45) Date of Patent: May 18, 2021

(54) CRACKING AEROSOL COMPOSITION

(71) Applicant: TOYO AEROSOL INDUSTRY CO., LTD., Tokyo (JP)

(72) Inventor: Yoshino Iizuka, Tokyo (JP)

(73) Assignee: TOYO AEROSOL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 16/569,781

(22) Filed: Sep. 13, 2019

(65) Prior Publication Data

US 2020/0000691 A1 Jan. 2, 2020

Related U.S. Application Data

(63) Continuation of application No. PCT/JP2017/016881, filed on Apr. 28, 2017.

(51) Int. Cl.

| | | |
|---|---|---|
| A61K 8/04 | (2006.01) | |
| A61Q 7/00 | (2006.01) | |
| A61K 33/00 | (2006.01) | |
| A61K 9/107 | (2006.01) | |
| A61K 9/12 | (2006.01) | |
| A61K 8/06 | (2006.01) | |
| A61K 8/19 | (2006.01) | |
| A61K 8/34 | (2006.01) | |
| A61K 8/31 | (2006.01) | |
| A61K 47/10 | (2017.01) | |
| A61K 47/06 | (2006.01) | |
| A61K 47/14 | (2017.01) | |
| A61K 47/26 | (2006.01) | |
| A61K 8/86 | (2006.01) | |

(52) U.S. Cl.
CPC ............... *A61K 8/046* (2013.01); *A61K 8/06* (2013.01); *A61K 8/19* (2013.01); *A61K 8/31* (2013.01); *A61K 8/34* (2013.01); *A61K 8/86* (2013.01); *A61K 9/107* (2013.01); *A61K 9/122* (2013.01); *A61K 33/00* (2013.01); *A61K 47/06* (2013.01); *A61K 47/10* (2013.01); *A61K 47/14* (2013.01); *A61K 47/26* (2013.01); *A61Q 7/00* (2013.01)

(58) Field of Classification Search
None
See application file for complete search history.

(56) References Cited

U.S. PATENT DOCUMENTS

| | | | |
|---|---|---|---|
| 2013/0078191 A1 | 3/2013 | Teramoto et al. | |
| 2014/0246515 A1* | 9/2014 | Nakajima | A61K 8/342 239/307 |

FOREIGN PATENT DOCUMENTS

| | | |
|---|---|---|
| JP | S58-189106 A | 11/1983 |
| JP | S61-153170 A | 7/1986 |
| JP | 2000345146 A | 12/2000 |
| JP | 2001335468 A | 12/2001 |
| JP | 2003-055187 A | 2/2003 |
| JP | 2003335629 A | 11/2003 |
| JP | 2012017464 A | 1/2012 |
| JP | 2014-062208 A | 4/2014 |
| JP | 2015101545 A * | 6/2015 |
| JP | 2015101545 A | 6/2015 |

OTHER PUBLICATIONS

English Language Translation of JP 2015 101545. (Year: 2015).*
U.S. Appl. No. 16/569,781, filed Dec. 8, 2020 Response, Exhibit A. (Year: 2020).*
International Search Report dated Jun. 6, 2017 for PCT/JP2017/016881 and English translation.
EPO, Extended European Search Report for the corresponding European patent application No. 17907690.6, dated Jan. 7, 2020.
JPO, Machine English translation of JP 2015-101545 A, retrieved Sep. 9, 2020.
Office Action (Notification of Reasons for Refusal) for corresponding Japanese Application No. 2019-515010 dated Aug. 25, 2020 with English translation (10 pages).

* cited by examiner

*Primary Examiner* — Dominic Lazaro

(74) *Attorney, Agent, or Firm* — Lucas & Mercanti, LLP

(57) ABSTRACT

The present invention has as its object the provision of a cracking aerosol composition in which, despite containing carbon dioxide, a foam-breaking sound is generated in a viscous flowable discharge by the action of the carbon dioxide and a liquefied petroleum gas.

A cracking aerosol composition of the present invention is a cracking aerosol composition to be filled in an aerosol container including a pressure-resistant container having an aerosol valve, wherein
the aerosol composition includes a liquefied petroleum gas, water, a lower alcohol, carbon dioxide, an emulsifier, an emulsifying aid and a thickener; the proportion of the liquefied petroleum gas is 45.0 to 73.0 mass %, the proportion of the lower alcohol is 4.0 to 12.0 mass %, the proportion of the carbon dioxide is 0.1 to 3.5 mass % and the proportion of the emulsifier is 0.02 to 1.2 mass %; and the emulsifier includes two types of nonionic surfactants having different HLB values, and the mass ratio of the two types of nonionic surfactants is 1:10 to 10:1.

5 Claims, No Drawings

CRACKING AEROSOL COMPOSITION

CROSS REFERENCE TO RELATED APPLICATIONS

This Application is a continuation of PCT/JP2017/016881 filed on Apr. 28, 2017, which is incorporated herein by reference.

TECHNICAL FIELD

The present invention relates to cracking aerosol compositions and more particularly to a cracking aerosol composition containing carbon dioxide.

BACKGROUND ART

Conventionally, as a certain type of aerosol composition, there is known a foam-breaking foam-forming aerosol composition in which a foamy discharge that produces a foam-breaking sound is formed (for example, see Patent Literature 1).

Such a foam-breaking foam-forming aerosol composition contains a liquefied petroleum gas, water, a surfactant, an emulsifying aid, and the like, together with components according to the intended use application. The characteristics of the formed foam to break with a foam-breaking sound, that is, the cracking characteristics, the feeling of use in the case of being applied to the human body, and the like greatly vary depending on the types and proportions of the liquefied petroleum gas, the surfactant and the emulsifying aid.

On the other hand, an aerosol composition containing carbon dioxide is known as an aerosol composition by which a foamy (non-foam-breaking foam) discharge is formed.

Such an aerosol composition containing carbon dioxide is suitably used as a hair growth agent, a massaging agent, or the like, since the blood circulation promoting effect by carbon dioxide is expected.

Thus, when the inventors of the present invention attempted to incorporate carbon dioxide into cracking aerosol compositions, it was revealed that sufficient investigation was necessary. More specifically, for example, it has been revealed that the simple incorporation of carbon dioxide into a known cracking aerosol composition causes various disadvantages such as the inability to produce a sufficiently large foam-breaking sound.

CITATION LIST

Patent Literature

Patent Literature 1: Japanese Patent Application Laid-Open No. 2003-335629

SUMMARY OF INVENTION

Technical Problem

The present invention has been made in view of the foregoing circumstances and has as its object the provision of a cracking aerosol composition in which, despite containing carbon dioxide, a foam-breaking sound is generated in a viscous flowable discharge by the action of the carbon dioxide and a liquefied petroleum gas.

Solution to Problem

A cracking aerosol composition of the present invention is a cracking aerosol composition to be filled in an aerosol container including a pressure-resistant container having an aerosol valve, wherein the aerosol composition includes a liquefied petroleum gas, water, a lower alcohol, carbon dioxide, an emulsifier, an emulsifying aid and a thickener, the proportion of the liquefied petroleum gas is 45.0 to 73.0 mass %, the proportion of the lower alcohol is 4.0 to 12.0 mass %, the proportion of the carbon dioxide is 0.1 to 3.5 mass % and the proportion of the emulsifier is 0.02 to 1.2 mass %, and the emulsifier includes two types of nonionic surfactants having different HLB values, and the mass ratio of the two types of nonionic surfactants is 1:10 to 10:1.

In the cracking aerosol composition of the present invention, it is preferable that the two types of nonionic surfactants constituting the emulsifier include a first nonionic surfactant having an HLB value of 15.0 to 18.0 and a second nonionic surfactant having an HLB value of 10.0 to 15.0, and the difference in HLB value between the first nonionic surfactant and the second nonionic surfactant is 1.0 to 5.0.

In the cracking aerosol composition of the present invention having such a configuration, it is preferable that the first nonionic surfactant is at least one selected from the group consisting of polyoxyethylene coconut oil fatty acid sorbitan and polyoxyethylene sorbit monolaurate, and that the second nonionic surfactant is at least one selected from the group consisting of polyoxyethylene sorbit tetraoleate and a polyoxyethylene hardened castor oil.

In the cracking composition of the present invention, it is preferable that the viscosity at a temperature of 20° C. of a liquid concentrate containing the water, the lower alcohol, the emulsifier, the emulsifying aid and the thickener is 50 to 1000 mPa·s.

Advantageous Effects of Invention

In the cracking aerosol composition of the present invention, two types of nonionic surfactants having different HLB values are used in combination in a specific mass ratio as emulsifiers, and the emulsifiers, the lower alcohol, the liquefied petroleum gas and carbon dioxide are contained in respective specific proportions. Therefore, even if carbon dioxide is contained, the emulsifying action by the emulsifier is sufficiently exhibited, and so a good emulsified state can be obtained. In addition, since the obtained discharge is a viscous fluid discharge, carbon dioxide and the liquefied petroleum gas are vaporized in the fluid discharge to gradually cause foaming, and the foam formed by the foaming is spontaneously broken, thereby causing a foam-breaking sound.

Accordingly, in the cracking aerosol composition of the present invention, sufficient cracking characteristics are obtained in the viscous flowable discharge by the action of the carbon dioxide and liquefied petroleum gas, even though the cracking aerosol composition contains carbon dioxide. As a result, it is possible to obtain a favorable feeling of use when the cracking aerosol composition of the present invention is applied to the human body.

Further, in the cracking aerosol composition of the present invention, when two types of nonionic surfactants having specific HLB values and a difference in HLB value between them falling within a specific range are selectively used in combination as emulsifiers, more excellent emulsifying easiness and emulsifying stability, and further excellent cracking characteristics can be obtained. In particular, in the case of application to the human body, since the amount of the emulsifier used can be made small, occurrence of a sticky feeling can be suppressed, and therefore, a more favorable feeling of use can be obtained.

DESCRIPTION OF EMBODIMENTS

The cracking aerosol composition of the present invention contains a liquefied petroleum gas, a lower alcohol, carbon dioxide and an emulsifier in respective specific proportions, and also contains water, an emulsifying aid and a thickener. The cracking aerosol composition is filled into an aerosol container including a pressure-resistant container having an aerosol valve to be produced as an aerosol product.

In the cracking aerosol composition of the present invention, not only the liquefied petroleum gas and carbon dioxide constitute a gas phase as a propellant, but also a part of the liquefied petroleum gas and a part of the carbon dioxide constitute a liquid phase together with a liquid concentrate containing water, the thickener, the emulsifier and the emulsifying aid. In the discharge, a foam-breaking sound is generated by the action of the liquefied petroleum gas and carbon dioxide. More specifically, the cracking aerosol composition of the present invention forms a viscous flowable discharge, and in the resulting flowable discharge, carbon dioxide and liquefied petroleum gas are vaporized to cause the discharge to gradually foam. Then, the foam formed by the foaming is spontaneously broken to generate a foam-breaking sound. In other words, it has cracking characteristics (i.e., characteristics in which the formed foam breaks with a foam-breaking sound).

The cracking aerosol composition of the present invention is characterized in that the proportion of the liquefied petroleum gas is 45.0 to 73.0 mass %, the proportion of the lower alcohol is 4.0 to 12.0 mass %, the proportion of the carbon dioxide is 0.1 to 3.5 mass %, and the proportion of the emulsifier is 0.02 to 1.2 mass %. The cracking aerosol composition of the present invention is characterized in that the emulsifier includes two types of nonionic surfactants having different HLB values (Hydrophile-Lipophile Balance: balance between hydrophilic and lipophilic properties) and the mass ratio of the two types of nonionic surfactants is 1:10 to 10:1.

In the cracking aerosol composition of the present invention, the respective proportions of the liquefied petroleum gas, lower alcohol, carbon dioxide and emulsifier are appropriately determined within the above-mentioned ranges in accordance with the use application or the like in relation to other constituent components.

Specifically, for example, when the proportion of the liquefied petroleum gas is relatively large, the proportion of the emulsifier may preferably be relatively large, and the proportion of the lower alcohol may preferably be relatively small. In such a case, it is preferable that the proportion of the emulsifying aid is large.

When the proportion of the lower alcohol is relatively large, it is preferable that the proportion of the emulsifier is relatively large. In such a case, it is preferable that the proportion of the thickener is large. The proportion of the lower alcohol may preferably be relatively large when the proportion of the emulsifying aid is large.

When the proportion of the emulsifier is relatively large, it is preferable that the proportion of the lower alcohol is relatively large. In such a case, it is preferable that the proportion of the thickener is small. The proportion of the emulsifier may preferably be relatively large when the proportion of the emulsifying aid is small.

Hereinafter, components constituting the cracking aerosol composition of the present invention will be described.

In the cracking aerosol composition of the present invention, the liquid phase comprises an oily phase containing a part of the liquefied petroleum gas dissolved in the lower alcohol and an aqueous phase containing water having viscosity imparted thereto by the thickener and in which apart of carbon dioxide is dissolved. The liquid phase is an oil-in-water (O/W) emulsion in which dispersed particles of the oily phase are uniformly dispersed in a dispersion medium of the aqueous phase by the action of the emulsifier and the emulsifying aid.

Water:

Purified water is used as the water which is an essential component.

The proportion of water is appropriately determined in accordance with the proportions of the other components to constitute the cracking aerosol composition in consideration of the use application of the cracking aerosol composition and the like.

Lower Alcohol:

The lower alcohol, which is an essential component, functions as a solvent for the liquefied petroleum gas. In particular, when the cracking aerosol composition is applied to the human body, a cooling effect and a non-residual sensation effect are exhibited at the application site.

As examples of the lower alcohols, may be mentioned alcohols having 1 to 5 carbon atoms, such as ethanol, 1-propanol and 2-propanol. These may be used either singly or in any combination thereof.

Among these, ethanol may be preferable because solubility and cracking characteristics of the liquefied petroleum gas can be reliably obtained. Further, when the cracking aerosol composition is used as a composition for the human body, use of ethanol as the lower alcohol can provide a good feeling of use from the viewpoints of cooling property, non-residual feeling property, and the like.

The proportion of the lower alcohol is 4.0 to 12.0 mass %, preferably 4.0 to 11.0 mass %, in the entire cracking aerosol composition.

If the proportion of the lower alcohol is too large, there is a possibility that good emulsifying stability may not be obtained in the composition.

On the other hand, when the proportion of the lower alcohol is too small, there is a possibility that a viscous flowable discharge may not be obtained because a sufficient freezing point lowering action by the lower alcohol is not obtained. More specifically, there is a possibility that the discharge becomes a sherbet shape due to freezing of water in the discharge. In addition, there is a possibility that the liquefied petroleum gas may not be sufficiently dissolved in the liquid concentrate (specifically, in the lower alcohol constituting the liquid concentrate), and due to this, a good emulsified state may not be obtained. In particular, there is a possibility that, when it is applied to the skin surface as a composition for the human body, a good feeling of use may not be obtained due to the fact that the feeling of stickiness occurs at the application site.

Emulsifier:

The emulsifier, which is an essential component, has a function of dispersing dispersed particles of the oily phase in a dispersion medium of the aqueous phase.

The emulsifier is composed of two types of nonionic surfactants having different HLB values.

In this emulsifier, the mass ratio of the two types of nonionic surfactants may preferably be 1:10 to 10:1, more preferably 1:5 to 5:1.

In the cracking aerosol composition of the present invention, the two types of nonionic surfactants having different HLB values are used in combination as an emulsifier. Thus, the emulsifying action by the emulsifier is sufficiently exhibited even in the presence of carbon dioxide, and so a good emulsified state can be obtained. When the mass ratio of the two types of nonionic surfactants falls within the aforementioned range, good emulsifying stability can be obtained in the cracking aerosol composition.

The two types of nonionic surfactants constituting the emulsifier may preferably be composed of a first nonionic surfactant having an HLB value of 15.0 to 18.0 and a second nonionic surfactant having an HLB value of 10.0 to 15.0, and may preferably have a difference of 1.0 to 5.0 between the HLB value of the first nonionic surfactant and the HLB value of the second nonionic surfactant.

When the two types of nonionic surfactants having specific HLB values and a difference in HLB value between them falling within a specific range are used in combination, there can be provided a better emulsifying effect. Therefore, it is possible to obtain more excellent emulsifying easiness and emulsifying stability as well as more excellent cracking characteristics. In particular, in the case of application to the human body, since the amount of the emulsifier used can be made small, the occurrence of a sticky feeling can be suppressed, and therefore, a favorable feeling of use can be obtained.

Thus, if the difference between the HLB value of the first nonionic surfactant and the HLB value of the second nonionic surfactant is too large or too small, there is a possibility that a good emulsified state and emulsifying stability may not be obtained in either case.

Specific examples of the first nonionic surfactant include polyoxyethylene sorbitan fatty acid esters such as polyoxyethylene (20) sorbitan monolaurate (HLB value: 16.7), polyoxyethylene (20) sorbitan monopalmitate (HLB value: 15.6) and polyoxyethylene (20) coconut oil fatty acid sorbitan (HLB value: 16.9), polyoxyethylene alkyl ethers such as polyoxyethylene (25) octyldodecyl ether (HLB value: 15.7), polyoxyethylene sorbit fatty acid esters such as polyoxyethylene (6) sorbit monolaurate (HLB value: 15.5), polyoxyethylene lanolin alcohols such as polyoxyethylene (40) lanolin alcohol (HLB value: 17.0), polyethylene glycol fatty acid esters such as polyethylene glycol distearate (HLB value: 16.5), polyoxyethylene sterols such as polyoxyethylene (20) phytosterol (HLB value: 15.5) and polyoxyethylene alkyl ether phosphoric acid such as polyoxyethylene lauryl ether (10) sodium phosphate (HLB value: 17.0).

Specific examples of the second nonionic surfactant include polyoxyethylene sorbitan fatty acid esters such as polyoxyethylene (85) sorbitan trioleate (HLB value: 11.0) and polyoxyethylene (65) sorbitantristearate (HLB value: 10.5), polyoxyethylene sorbit fatty acid esters such as polyoxyethylene (60) sorbit tetraoleate (HLB value: 14.0), polyoxyethylene alkyl ethers such as polyoxyethylene (10) cetyl ether (HLB value: 13.5) and polyoxyethylene (10) oleyl ether (HLB value: 14.5), polyoxyethylene hydrogenated castor oils such as polyoxyethylene higher alcohol ether (HLB value: 10.5 to 13.3) and polyoxyethylene (40) hydrogenated castor oil (HLB value: 12.5), polyglycerin fatty acid esters such as decaglyceryl monomyristate (HLB value: 14.5), polyoxyethylene lanolin such as polyoxyethylene (10) lanolin (HLB value: 12.0), polyoxyethylene alkyl ether phosphoric acid/phosphate such as sodium polyoxyethylene (8) oleyl ether phosphate (HLB value: 12.5) and sodium polyoxyethylene (4) lauryl ether phosphate (HLB value: 13.0), polyethylene glycol fatty acid esters such as polyethylene (10) glycol monolaurate (HLB value: 12.5), polyoxyethylene glycerin fatty acid esters such as polyoxyethylene (15) glyceryl monostearate (HLB value: 13.5) and polyoxyethylene sterols such as polyoxyethylene (10) phytosterol (HLB value: 12.5).

As a preferable combination of the first nonionic surfactant and the second nonionic surfactant, it is preferable that the first nonionic surfactant is at least one selected from the group consisting of polyoxyethylene coconut oil fatty acid sorbitan and polyoxyethylene sorbit monolaurate, and the second nonionic surfactant is at least one selected from the group consisting of polyoxyethylene sorbit tetraoleate and polyoxyethylene (40) hydrogenated castor oil.

Specifically, it is preferable to use polyoxyethylene (20) coconut oil fatty acid sorbitan as the first nonionic surfactant and polyoxyethylene (60) sorbit tetraoleate as the second nonionic surfactant, or use polyoxyethylene (6) sorbit monolaurate as the first nonionic surfactant, and polyoxyethylene (40) hydrogenated castor oil as the second nonionic surfactant.

In the first nonionic surfactant and the second nonionic surfactant, as described above, the mass ratio, specifically, the ratio of the proportion of the first nonionic surfactant in the cracking aerosol composition and the proportion of the second nonionic surfactant in the cracking aerosol composition (the first nonionic surfactant: the second nonionic surfactant) may preferably be 1:10 to 10:1, more preferably 1:5 to 5:1.

The proportion of the emulsifier is 0.02 to 1.2 mass %, preferably 0.20 to 0.80 mass %, in the entire cracking aerosol composition.

If the proportion of the emulsifier is too large, there is a possibility that the discharge may become foamy and the cracking characteristic may not be obtained. In particular, when it is applied to the skin surface as a composition for the human body, there is a possibility that a good feeling of use may not be obtained due to a feeling of stickiness or a strong skin irritation at the application site.

On the other hand, if the proportion of the emulsifier is too small, there is a possibility that an emulsified state may not be obtained in the composition (liquid concentrate).

Emulsifying Aid:

The emulsifying aid, which is an essential component, is a powder, exists in a dispersed state in the liquid phase, and has a function of facilitating dispersion of the dispersed particles of the oily phase in a dispersion medium of the aqueous phase, and a function of improving the stability of the dispersed state, that is, the emulsifying stability.

As examples of the material of the powder constituting the emulsifying aid, maybe mentioned silica, talc, alumina, zeolite and polyamide (nylon).

As the powder constituting the emulsifying aid in the cracking aerosol composition of the present invention, silica may be preferable.

The average particle size of the powder constituting the emulsifying aid may preferably be 1 to 30 μm.

If the average particle size of the fine particles constituting the emulsifying aid is too large, there is a possibility that a rough feeling may occur at the application site particularly when the cracking aerosol composition is applied to the skin surface as a composition for the human body.

On the other hand, if the average particle size of the fine particles constituting the emulsifying aid is too small, there is a possibility that the cracking aerosol composition may adversely affect the human body particularly when it is applied to the skin surface as a composition for human body use.

The proportion of the emulsifying aid may preferably be 0.04 to 0.4 mass % in the entire cracking aerosol composition.

If the proportion of the emulsifying aid is too large, clogging of the aerosol valve tends to occur, and there is a possibility that a good feeling of use may not be obtained particularly when the cracking aerosol composition is applied to the skin surface as a composition for the human body, because sense of roughness is generated at the application site.

On the other hand, if the proportion of the emulsifying aid is too small, there is a possibility that the emulsifying easiness may not be obtained. In particular, long shaking periods may be required to obtain a good emulsified state in the cracking aerosol composition.

Thickener:

The thickener, which is an essential component, mainly adjusts the viscosity of the discharge, and has a function of adjusting the level of the crackling sound generated when the foam formed by the foaming gradually generated in the flowable discharge is spontaneously broken, and also has a function of improving the adhesiveness of the discharge to the application site. The thickener also has a function of facilitating dispersion of dispersed particles of the oily phase in a dispersion medium of the aqueous phase by adjusting the viscosity of the cracking aerosol composition (liquid concentrate).

As the thickener, a cellulose-based macromolecule and a water-soluble macromolecule such as a gum substance may be used.

As the examples of the cellulose-based macromolecule constituting the thickener, may be mentioned hydroxyethylcellulose, hydroxypropylcellulose, hydroxypropylmethylcellulose, sodium carboxymethylcellulose, nitrocellulose and crystalline cellulose.

As the examples of the gum substances constituting the thickener, may be mentioned xanthan gum, carrageenan, gum arabic, gum tragacanth, cationized guar gum, guar gum, gellan gum and locust beam gum.

As the thickener in the cracking aerosol composition of the present invention, one type of water-soluble macromolecule may be used solely, or two or more types of water-soluble macromolecules maybe used in any combination.

The proportion of the thickener may preferably be 0.04 to 0.4 mass % in the entire cracking aerosol composition.

If the proportion of the thickener is too large, the viscosity of the cracking aerosol composition (liquid concentrate) becomes too large, and as a consequence, the dispersed particles of the oily phase may not be sufficiently dispersed in the dispersion medium of the aqueous phase. Therefore, there is a possibility that a good emulsified state may not be obtained in the cracking aerosol composition. In addition, there is a possibility that a good discharged state may not be obtained. Specifically, there is a possibility that the discharging itself may not be performed, or that the discharge in a desired amount may not be obtained. Further, there is a possibility that a feeling of stickiness may occur particularly in application to the human body, and a favorable feeling of use may not be obtained.

On the other hand, when the proportion of the thickener is too small, the viscosity of the cracking aerosol composition (liquid concentrate) becomes too small, and as a consequence, a good emulsified state may not be obtained in the cracking aerosol composition. Thus, there is a possibility that cracking characteristics may not be obtained in the discharge.

Liquefied Petroleum Gas:

The liquefied petroleum gas, which is an essential component, constitutes the liquid phase by dissolving a part thereof in the lower alcohol, and also forms the gas phase as a propellant together with carbon dioxide (specifically, a part of carbon dioxide) by another part thereof.

Specific examples of the liquefied petroleum gases include, for example, a mixture of propane, n-butane and iso-butane. The liquefied petroleum gas may contain n-pentane and iso-pentane.

The proportion of the liquefied petroleum gas is 45.0 to 73.0 mass %, preferably 48.0 to 70.0 mass %, in the entire cracking aerosol composition.

If the proportion of the liquefied petroleum gas is too large, there is a possibility that an emulsified state may not be obtained in the composition.

On the other hand, if the proportion of the liquefied petroleum gas is too small, there is a possibility that the discharge may become foamy and cracking characteristics may not be obtained.

Carbon Dioxide:

Since carbon dioxide, which is an essential component, has solubility in water, apart thereof constitutes the liquid phase by being dissolved in water having viscosity imparted thereto by the thickener, and another part thereof forms the gas phase as a propellant together with the liquefied petroleum gas (specifically, a part of the liquefied petroleum gas).

The proportion of carbon dioxide is 0.1 to 3.5 mass %, preferably 0.8 to 1.5 mass %, in the entire cracking aerosol composition.

If the proportion of carbon dioxide is too large, there is a possibility that sufficient safety may not be obtained due to too large internal pressure of the product in the aerosol container.

Here, in the cracking aerosol composition of the present invention, the internal pressure of the product in the aerosol container may preferably be not more than 0.8 MPa, more preferably 0.3 to 0.7 MPa, at a temperature of 35° C.

When the internal pressure of the product is too high, there is a possibility that sufficient safety may not be obtained due to too high filling pressure of the propellant (specifically, liquefied petroleum gas and carbon dioxide).

Thus, the product internal pressure of 0.3 to 0.7 MPa at a temperature of 35° C. in the aerosol container can provide sufficient safety required for the aerosol product as well as sufficient cracking characteristics for the discharge.

Optional Components:

The cracking aerosol composition of the present invention may contain, in addition to the essential components (specifically, water, lower alcohol, emulsifier, emulsifying aid, thickener, liquefied petroleum gas and carbon dioxide), optional components as necessary. Specific examples thereof include, for example, a humectant, a fungicide and a preservative, a skin protectant (amino acid), vitamins, various extracts, a deodorant, a cooling agent and the like.

As examples of the humectants constituting the optional components, may be mentioned propylene glycol, glycerin, 1,3-butylene glycol, collagen, xylitol, sorbitol, hyaluronic acid, sodium lactate, keratin, casein, lecithin and urea.

As examples of the fungicides and preservatives constituting the optional components, may be mentioned paraoxybenzoic acid esters, sodium benzoate, phenoxyethanol, benzalkonium chloride, benzethonium chloride, chlorhexidine and chlorhexidine chloride.

As examples of the skin protectants (amino acid) constituting the optional component, maybe mentioned glycine, alanine, isoleucine, leucine, serine, tryptophan, cystine, methionine, aspartic acid, glutamic acid and arginine. As examples of the vitamins constituting optional components, may be mentioned retinol, retinol palmitate, pyridoxine hydrochloride, tocopherol acetate, vitamin $D_2$, pantothenic acid and biotin.

As examples of the various extracts constituting the optional components, may be mentioned peony extract, luffa cylindrica extract, rose extract, lemon extract, aloe extract, calamus root extract, eucalyptus extract, sage extract, tea extract, seaweed extract, placenta extract and silk extract.

As examples of the deodorants constituting the optional components, may be mentioned lauryl methacrylate, geranil crotolate, acetophenone myristate, benzyl acetate, benzyl propionate, methyl benzoate and methyl phenylacetate.

As examples of the cooling agent constituting the optional components, may be mentioned 1-menthol and d,l-camphor.

In the cracking aerosol composition constituted by the above-mentioned essential components and optional components, the viscosity of the liquid concentrate at a temperature of 20° C. may preferably be 50 to 1000 mPa·s, more preferably 80 to 300 mPa·s.

When the viscosity of the liquid concentrate is too high, there is a possibility that a good discharge state may not be obtained. Specifically, there is a possibility that the discharge itself may not be performed, or that the discharge in a desired amount may not be obtained. In addition, particularly in the case of application to the human body, there is a possibility that a feeling of stickiness may occur and a good feeling of use may not be obtained.

On the other hand, if the viscosity of the liquid concentrate is too small, there is a possibility that a good emulsified state may not be obtained, and sufficient cracking characteristics may not be obtained.

The cracking aerosol compositions of the present invention with such a configuration can be produced by filling and shaking, in an aerosol container, essential components (specifically, water, lower alcohol, emulsifier, emulsifying aid, thickener, liquefied petroleum gas and carbon dioxide) and optional components contained as necessary.

In such a cracking aerosol composition of the present invention, two types of nonionic surfactants having different HLB values are used in combination at a specific mass ratio as an emulsifier, and the emulsifier, lower alcohol, liquefied petroleum gas and carbon dioxide are contained in respective specific proportions, and so even when carbon dioxide is contained, the emulsifying action by the emulsifier is sufficiently exhibited. Therefore, a good emulsified state can be obtained. In addition, since the obtained discharge is a viscous fluid discharge, the carbon dioxide and the liquefied petroleum gas are vaporized in the fluid discharge to gradually generate foam, and the foam formed by the foaming is spontaneously broken, thereby causing a foam-breaking sound.

Accordingly, in the cracking aerosol composition of the present invention, sufficient cracking characteristics are obtained in the viscous flowable discharge by the action of the carbon dioxide and the liquefied petroleum gas, even when the cracking aerosol composition contains carbon dioxide.

Further, in the cracking aerosol composition of the present invention, particularly when it is applied to the human body, a refreshing feeling can be obtained by the cracking characteristics, and so a good feeling of use can be obtained.

Herein, in the cracking aerosol composition containing carbon dioxide, the matter that the above-mentioned effect can be obtained by using two types of nonionic surfactants having different HLB values as emulsifiers at a specific mass ratio, and by using the lower alcohol, emulsifier, liquefied petroleum gas and carbon dioxide in respective specific proportions has been clarified by the results of experiments conducted by the inventors for the first time.

In the cracking aerosol composition of the present invention, two types of nonionic surfactants having specific HLB values and a difference in HLB value between them falling within a specific range are used in combination as emulsifiers. Therefore, emulsifying stability can be obtained and further excellent cracking characteristics can be obtained. In particular, in the case of application to the human body, the occurrence of a sticky feeling at the application site on the skin is suppressed, and therefore, a more favorable feeling of use can be obtained.

The cracking aerosol composition of the present invention can be used, for example, as a composition for the human body or for various other applications. Furthermore, the composition can provide a good feeling of use without stickiness or skin irritation, contains carbon dioxide, and is expected to have a blood circulation promoting effect by carbon dioxide. Therefore, the composition can be suitably used particularly as a composition for the human body.

Specifically, the composition can be used as a hair growth agent, a massaging agent, a hair styling agent, a hair treatment agent, a shampoo agent and a conditioner agent.

EXAMPLES

Examples of the present invention will be described below, but the present invention is not limited thereto.

Examples 1 to 12 and Comparative Examples 1 to 7

First, the composition materials shown in Tables 1 and 2 were prepared, and the liquid concentrate was prepared by mixing the composition materials except for the liquefied petroleum gas and carbon dioxide in the proportions shown in Tables 1 and 2.

Next, the obtained liquid concentrate, liquefied petroleum gas (0.15 MPa) and carbon dioxide were filled in an aerosol container formed of a transparent pressure-resistant container made of glass and equipped with an aerosol valve in the proportions shown in Tables 1 and 2 so that the mass of the contents became 40 g, thereby producing an aerosol product for evaluation.

In the obtained plurality of aerosol products for evaluation, the internal pressure of the products at a temperature of 35° C. fell within the range of 0.3 to 0.7 MPa.

Here, in the obtained aerosol product for evaluation according to Example 1, the mass ratio (nonionic surfactant (1): nonionic surfactant (3)) of the two types of nonionic surfactants is 1:2, and the difference in HLB value between the nonionic surfactant (1) as the first nonionic surfactant and the nonionic surfactant (3) as the second nonionic surfactant is 2.9.

In each of the obtained aerosol products for evaluation according to Example 2, Example 4, Example 9, Example 11 and Example 12, the mass ratio (nonionic surfactant (1) : nonionic surfactant (3)) of the two types of nonionic surfactants is 1:1, and the difference in HLB value between the nonionic surfactant (1) as the first nonionic surfactant and the nonionic surfactant (3) as the second nonionic surfactant is 2.9.

In the obtained aerosol product for evaluation according to Example 3, the mass ratio (nonionic surfactant (1) : nonionic surfactant (3)) of the two types of nonionic surfactants is 5:1, and the difference in HLB value between the nonionic surfactant (1) as the first nonionic surfactant and the nonionic surfactant (3) as the second nonionic surfactant is 2.9.

In the obtained aerosol product for evaluation according to Example 5, the mass ratio (nonionic surfactant (1) : nonionic surfactant (3)) of the two types of nonionic surfactants is 1:5, and the difference in HLB value between the nonionic surfactant (1) as the first nonionic surfactant and the nonionic surfactant (3) as the second nonionic surfactant is 2.9.

In each of the obtained aerosol products for evaluation according to Example 6 and Example 8, the mass ratio (nonionic surfactant (1) : nonionic surfactant (3)) of the two types of nonionic surfactants is 2:1, and the difference in HLB value between the nonionic surfactant (1) as the first nonionic surfactant and the nonionic surfactant (3) as the second nonionic surfactant is 2.9.

In the obtained aerosol product for evaluation according to Example 7, the mass ratio (nonionic surfactant (2) : nonionic surfactant (4)) of the two types of nonionic surfactants is 2:1, and the difference in HLB value between the nonionic surfactant (2) as the first nonionic surfactant and the nonionic surfactant (4) as the second nonionic surfactant is 3.0.

In the obtained aerosol product for evaluation according to Example 10, the mass ratio (nonionic surfactant (1) : nonionic surfactant (5)) of the two types of nonionic surfactants is 1:1, and the difference in HLB value between the nonionic surfactant (1) and the nonionic surfactant (5) is 8.3.

Each of the obtained aerosol products for evaluation was evaluated as follows. The results are shown in Tables 1 and 2.

Emulsion formability: emulsifying easiness:

The obtained aerosol product for evaluation was evaluated for emulsion formability (emulsifying easiness) under a temperature condition at room temperature (25° C.) (hereinafter, also referred to as "room temperature condition"). Specifically, the procedure to check whether or not an emulsion was formed (hereinafter referred to as the "emulsion formation confirmation procedure") by visually observing the aerosol container for each shaking by hand was repeated. Then, the number of shakings required before the emulsion was formed was confirmed.

Emulsion Reformability: Emulsifying Stability:

The obtained aerosol product for evaluation was shaken under the room temperature condition to form an emulsion, and then left to stand under the room temperature condition for one day. Thereafter, under the room temperature condition, the emulsion formation confirmation procedure was repeated to confirm the number of shakings required until the emulsion was formed, thereby evaluating the emulsion reformability (emulsifying stability).

Foam-Breaking Property: Cracking Characteristics:

The foam breaking property (cracking characteristics) was evaluated according to evaluation criteria by shaking the obtained aerosol product for evaluation under the room temperature condition for 30 seconds by hand and then discharging 1 g of the content to form a discharge followed by confirming the nature of the formed discharge. The composition is evaluated as "A" for having extremely favorable cracking characteristics of the discharge when foam is gradually generated in the discharge and all of the foam formed by the foaming is spontaneously broken with a crackling sound. The composition is evaluated as "B" for having certain cracking characteristics when foam is gradually generated in the discharge and a part of the foam formed by the foaming is spontaneously broken with a crackling sound while another part of the foam is not broken. The composition is evaluated as "C" for having no cracking characteristics while being formable when the discharge is in a foam state (non-cracking foam). The composition is evaluated as "D" for having no cracking characteristics when the discharge is in a sherbet state. The composition is evaluated as "E" for having no cracking characteristics when the discharge is neither foamy nor in a sherbet state and is in a liquid state.

TABLE 1

| | | | Example 1 | Example 2 | Example 3 | Example 4 | Example 5 | Example 6 |
|---|---|---|---|---|---|---|---|---|
| Composition | Emulsifier (Mass %) | Nonionic Surfactant (1) (HLB Value 16.9) | 0.14 | 0.21 | 0.35 | 0.21 | 0.07 | 0.28 |
| | | Nonionic Surfactant (2) (HLB Value 15.5) | — | — | — | — | — | — |
| | | Nonionic Surfactant (3) (HLB Value 14.0) | 0.28 | 0.21 | 0.07 | 0.21 | 0.35 | 0.14 |
| | | Nonionic Surfactant (4) (HLB Value 12.5) | — | — | — | — | — | — |
| | | Nonionic Surfactant (5) (HLB Value 8.6) | — | — | — | — | — | — |
| | Emulsifying Aid (Mass %) | Silica Powder (Average Particle Size 30 μm) | 0.35 | 0.35 | 0.35 | 0.35 | 0.35 | 0.35 |
| | Lower Alcohol (Mass %) | Ethanol | 7.00 | 7.00 | 7.00 | 7.00 | 7.00 | 7.00 |
| | Thickener (Mass %) | Xanthan Gum | 0.11 | 0.11 | 0.11 | 0.11 | 0.11 | 0.11 |
| | | Water (Mass %) | 42.12 | 42.12 | 42.12 | 22.12 | 42.12 | 42.12 |
| | | Liquefied Petroleum Gas (Mass %) | 49.00 | 49.00 | 49.00 | 69.00 | 49.00 | 47.00 |
| | | Carbon Dioxide (Mass %) | 1.00 | 1.00 | 1.00 | 1.00 | 1.00 | 3.00 |
| | | Total (Mass %) | 100.00 | 100.00 | 100.00 | 100.00 | 100.00 | 100.00 |
| | | Viscosity of Liquid Concentrate at 20° C. (mPa · s) | 150 | 150 | 160 | 150 | 150 | 150 |
| Evaluation | | Emulsion Formability | 5 | 5 | 4 | 7 | 5 | 5 |
| | | Emulsion Reformability | 3 | 3 | 4 | 4 | 4 | 4 |

TABLE 1-continued

|  |  |  | Example 7 | Example 8 | Example 9 | Example 10 | Example 11 | Example 12 |
|---|---|---|---|---|---|---|---|---|
| Composition | Emulsifier (Mass %) | Nonionic Surfactant (1) (HLB Value 16.9) | — | 0.28 | 0.21 | 0.21 | 0.21 | 0.01 |
|  |  | Nonionic Surfactant (2) (HLB Value 15.5) | 0.28 | — | — | — | — | — |
|  |  | Nonionic Surfactant (3) (HLB Value 14.0) | — | 0.14 | 0.21 | — | 0.21 | 0.01 |
|  |  | Nonionic Surfactant (4) (HLB Value 12.5) | 0.14 | — | — | — | — | — |
|  |  | Nonionic Surfactant (5) (HLB Value 8.6) | — | — | — | 0.21 | — | — |
|  | Emulsifying Aid (Mass %) | Silica Powder (Average Particle Size 30 μm) | 0.35 | 0.35 | 0.35 | 0.35 | 0.35 | 0.35 |
|  | Lower Alcohol (Mass %) | Ethanol | 7.00 | 7.00 | 7.00 | 7.00 | 7.00 | 7.00 |
|  | Thickener (Mass %) | Xanthan Gum | 0.11 | 0.11 | 0.18 | 0.11 | 0.11 | 0.11 |
|  | Water (Mass %) |  | 42.12 | 43.52 | 42.05 | 42.12 | 42.12 | 42.52 |
|  | Liquefied Petroleum Gas (Mass %) |  | 49.00 | 48.50 | 49.00 | 49.00 | 46.50 | 49.00 |
|  | Carbon Dioxide (Mass %) |  | 1.00 | 0.10 | 1.00 | 1.00 | 3.50 | 1.00 |
|  | Total (Mass %) |  | 100.00 | 100.00 | 100.00 | 100.00 | 100.00 | 100.00 |
|  | Viscosity of Liquid Concentrate at 20° C. (mPa·s) |  | 160 | 150 | 1000 | 160 | 150 | 120 |
| Evaluation | Emulsion Formability |  | 5 | 4 | 7 | 7 | 5 | 8 |
|  | Emulsion Reformability |  | 4 | 3 | 5 | 4 | 4 | 5 |
|  | Foam Breaking Property |  | A | A | B | B | B | B |

TABLE 2

|  |  |  | Comparative example 1 | Comparative example 2 | Comparative example 3 | Comparative example 4 | Comparative example 5 | Comparative example 6 | Comparative example 7 |
|---|---|---|---|---|---|---|---|---|---|
| Composition | Emulsifier (Mass %) | Nonionic Surfactant (1) (HLB Value 16.9) | 0.21 | 0.21 | 0.28 | 0.21 | 0.21 | 0.21 | 1.00 |
|  |  | Nonionic Surfactant(2) (HLB Value 15.5) | — | — | — | — | — | — | — |
|  |  | Nonionic Surfactant (3) (HLB Value 14.0) | 0.21 | — | 0.14 | 0.21 | 0.21 | 0.21 | 1.00 |
|  |  | Nonionic Surfactant (4) (HLB Value 12.5) | — | — | — | — | — | — | — |
|  |  | Nonionic Surfactant (5) (HLB Value 8.6) | — | — | — | — | — | — | — |
|  |  | Amphoteric Surfactant | — | 0.21 | — | — | — | — | — |
|  | Emulsifying Aid (Mass %) | Silica Powder (Average Particle Size 30 μm) | 0.35 | 0.35 | 0.35 | 0.35 | 0.35 | 0.35 | 0.35 |
|  | Lower Alcohol (Mass %) | Ethanol | 7.00 | 7.00 | 7.00 | 7.00 | 20.00 | 1.00 | 7.00 |
|  | Thickener (Mass %) | Xanthan Gum | 0.11 | 0.11 | 0.11 | 0.11 | 0.11 | 0.11 | 0.11 |
|  | Water (Mass %) |  | 62.12 | 22.12 | 42.12 | 12.12 | 29.12 | 48.12 | 40.54 |
|  | Liquefied Petroleum Gas (Mass %) |  | 29.00 | 69.00 | 50.00 | 79.00 | 49.00 | 49.00 | 49.00 |
|  | Carbon Dioxide (Mass %) |  | 1.00 | 1.00 | — | 1.00 | 1.00 | 1.00 | 1.00 |
|  | Total (Mass %) |  | 100.00 | 100.00 | 100.00 | 100.00 | 100.00 | 100.00 | 100.00 |
|  | Viscosity of Liquid Concentrate at 20° C. (mPa·s) |  | 150 | 140 | 150 | 150 | 100 | 180 | 210 |
| Evaluation | Emulsion Formability |  | 6 | 8 | 4 | 8 | 7 | 6 | 5 |
|  | Emulsion Reformability |  | 5 | 5 | 3 | 5 | 5 | 5 | 4 |
|  | Foam Breaking Property |  | C | D | A | D | E | D | C |

In Tables 1 and 2, the nonionic surfactant (1) is polyoxyethylene (20) coconut oil fatty acid sorbitan (HLB value: 16.9), and the nonionic surfactant (2) is polyoxyethylene (6) sorbit monolaurate (HLB value: 15.5). The nonionic surfactant (3) is polyoxyethylene (60) sorbit tetraoleate (HLB value: 14.0), and the nonionic surfactant (4) is polyoxyethylene (40) hydrogenated castor oil (HLB value: 12.5). The nonionic surfactant (5) is sorbitan coconut oil fatty acid (HLB value: 8.6), and the amphoteric surfactant is a lauryl dimethylamine oxide liquid.

From the above results, it was confirmed that according to the aerosol compositions of Examples 1 to 12 of the present invention, good emulsifying easiness and emulsifying stability were obtained despite containing carbon dioxide, and at the same time, a foam-breaking sound was generated in a viscous flowable discharge. It was confirmed that in the aerosol compositions according to Examples 1 to 12, the same cracking characteristics (foam-breaking property) as that of the aerosol composition (known foam-breaking foam-forming aerosol composition) in which carbon dioxide was not mixed was obtained, as apparent from comparison with the aerosol composition according to Comparative Example 3. Further, it was confirmed that in the aerosol compositions according to Examples 1 to 9, Example 11 and Example 12, since two types of nonionic surfactants having specific HLB values and a difference in HLB value between them falling within a specific range are selectively used as emulsifiers, better emulsifying stability and cracking characteristics were obtained, as apparent from comparison with the aerosol composition according to Example 2 and the aerosol composition according to Example 10.

Further, when the aerosol compositions according to Examples 1 to 12 were applied onto the skin, it was confirmed that good feeling of use was obtained because there was no feeling of stickiness at the application site.

The invention claimed is:

1. A cracking aerosol composition to be filled in an aerosol container including a pressure-resistant container having an aerosol valve, wherein
    the aerosol composition is under pressure and comprises a liquefied petroleum gas, carbon dioxide and a liquid concentrate,
    the liquid concentrate comprises water, a lower alcohol, an emulsifier, an emulsifying aid, and a thickener,
    a proportion of the liquefied petroleum gas is 45.0 to 73.0 mass %, a proportion of the lower alcohol is 4.0 to 12.0 mass %, a proportion of the carbon dioxide is 0.1 to 3.5 mass %, and a proportion of the emulsifier is 0.02 to 1.2 mass %,
    the emulsifier includes two types of nonionic surfactants having different HLB values, and a mass ratio of the two types of nonionic surfactants is 1:10 to 10:1, and
    the aerosol composition exhibiting a foam cracking sound during release from pressure.

2. The cracking aerosol composition according to claim 1, wherein
    the two types of nonionic surfactants constituting the emulsifier include a first nonionic surfactant having an HLB value of 15.0 to 18.0 and a second nonionic surfactant having an HLB value of 10.0 to 15.0, and a difference in HLB value between the first nonionic surfactant and the second nonionic surfactant is 1.0 to 5.0.

3. The cracking aerosol composition according to claim 2, wherein
    the first nonionic surfactant is at least one selected from the group consisting of polyoxyethylene coconut oil fatty acid sorbitan and polyoxyethylene sorbitan monolaurate, and
    the second nonionic surfactant is at least one selected from the group consisting of polyoxyethylene sorbitan tetraoleate and a polyoxyethylene (40) hydrogenated castor oil.

4. The cracking aerosol composition according to claim 1, wherein
    the liquid concentrate has a viscosity at a temperature of 20° C. from 50 to 1000 mPa·s.

5. The cracking aerosol composition according to claim 1, wherein
    the aerosol composition is disposed in an aerosol container including a pressure-resistant container having an aerosol valve.

* * * * *